(12) United States Patent
Luo et al.

(10) Patent No.: US 10,550,101 B2
(45) Date of Patent: Feb. 4, 2020

(54) CRYSTALLINE FORMS OF MESYLATE SALT OF PYRIDINYL AMINO PYRIMIDINE DERIVATIVE, PREPARATION METHODS THEREFOR, AND APPLICATIONS THEREOF

(71) Applicant: SHANGHAI ALLIST PHARMACEUTICAL AND MEDICAL TECHNOLOGY CORPORATIONS, Shanghai (CN)

(72) Inventors: Huibing Luo, Shanghai (CN); Qiang Zhang, Shanghai (CN)

(73) Assignee: SHANGHAI ALLIST PHARMACEUTICAL AND MEDICAL TECH CO, Shanghai (CN)

( * ) Notice: Subject to any disclaimer, the term of this patent is extended or adjusted under 35 U.S.C. 154(b) by 0 days.

(21) Appl. No.: 16/083,210

(22) PCT Filed: Mar. 1, 2017

(86) PCT No.: PCT/CN2017/000203
§ 371 (c)(1),
(2) Date: Sep. 7, 2018

(87) PCT Pub. No.: WO2017/152707
PCT Pub. Date: Sep. 14, 2017

(65) Prior Publication Data
US 2019/0092753 A1    Mar. 28, 2019

(30) Foreign Application Priority Data
Mar. 7, 2016    (CN) .......................... 2016 1 0127022

(51) Int. Cl.
*C07D 401/14*    (2006.01)
*A61P 35/00*    (2006.01)

(52) U.S. Cl.
CPC ............ *C07D 401/14* (2013.01); *A61P 35/00* (2018.01); *C07B 2200/13* (2013.01)

(58) Field of Classification Search
CPC .................................................. C07D 401/14
See application file for complete search history.

(56) References Cited

U.S. PATENT DOCUMENTS

| 8,946,235 B2 | 2/2015 | Butterworth et al. |
| 10,072,002 B2 * | 9/2018 | Luo ...................... A61K 31/506 |
| 2017/0210739 A1 | 7/2017 | Luo et al. |
| 2019/0100509 A1 * | 4/2019 | Luo ...................... C07D 401/14 |

FOREIGN PATENT DOCUMENTS

| CN | 103702990 A | 4/2014 |
| CN | 104761544 A | 7/2015 |
| CN | 105315259 A | 2/2016 |
| EP | 3181560 A1 | 6/2017 |
| WO | WO2016015453 A1 | 2/2016 |
| WO | WO2017152706 A1 | 9/2017 |

OTHER PUBLICATIONS

Solid State Characterization of Pharmaceuticals 63 (R.A. Storey et al., eds., 2011) (Year: 2011).*
J. Cruz-Cabeza et al., 44 Chemical Society Reviews, 8619-8635 (2015) (Year: 2015).*
International Search Report in Chinese with English translation on international application No. PCT/CN2017/000203, dated May 31, 2017, 6 pages.
Written Opinion in Chinese with English translation on international application No. PCT/CN2017/000203, dated May 31, 2017, 9 pages.
Supplemental European Search Report for European Application EP 17762393, dated Jun. 27, 2019, 5 pages.
Y. Nakai et al., "New Galenical Pharmacy", first edition, second printing, dated Apr. 25, 1984, pp. 102-104, 217-236.
Y. Shioji, "A Technique for Producing a Solid Preparation", Maruzen Co. Ltd., dated Jan. 27, 2003, pp. 9-14.
H. Yoshinaki, "Handbook for Organic Compound Crystal—Principle and Know-how," Maruzen Co. Ltd., dated Jul. 25, 2008, pp. 37-84.
"Experiment Chemistry, First edition, Basic operations I", fourth edition, edited by Japan Chemical Society, Marzen Co. Ltd., dated Apr. 5, 1996, pp. 184-186.
Japanese Office Action with English translation corresponding to JP application No. 2018547272, dated Aug. 13, 2019, 7 pages.

* cited by examiner

*Primary Examiner* — Alexander R Pagano
(74) *Attorney, Agent, or Firm* — Reising Ethington P.C.

(57) ABSTRACT

Forms I and II of the mesylate salt of the compound of formula (I), a preparation methods thereof, a pharmaceutical composition containing the crystal forms, and the use of the crystal forms in treating diseases mediated by activating and resistance mutations of EGFR, in particular cancer, in mammal, in particular in human. The crystal forms of the mesylate salt of the compound of formula (I) have good solubilities and high bioavailabilities in animals (I)

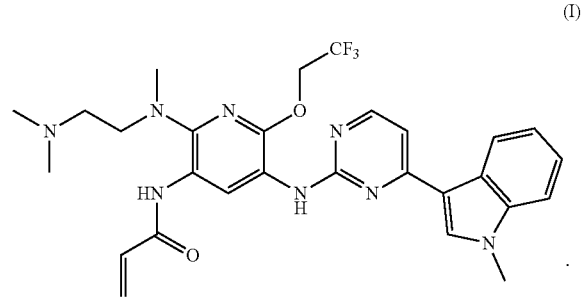

18 Claims, 5 Drawing Sheets

CRYSTALLINE FORMS OF MESYLATE SALT OF PYRIDINYL AMINO PYRIMIDINE DERIVATIVE, PREPARATION METHODS THEREFOR, AND APPLICATIONS THEREOF

TECHNICAL FIELD

The present invention relates to a mesylate salt of pyridinylaminopyrimidine derivative in crystal form. In particular, the present invention relates to a mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide in crystal form, the preparation method thereof, a pharmaceutical composition containing the crystal form, and the use of the crystal form in treating diseases mediated by activating and resistance mutations of EGFR, in particular cancer in mammal, in particular human.

BACKGROUND

Epidermal cell growth factors receptors (EGFR) are identified as one significant driving factor in the process for cellular growth and proliferation. The epidermal cell growth factors receptors family is composed of EGFR (Erb-B1), Erb-B2 (HER-2/neu), Erb-B3 and Erb-B4. The epidermal cell growth factor receptors are associated with the process for most cancers, such as lung cancer, colon cancer, breast cancer and the like. The overexpression and mutation of EGFR have been proved to be the leading risk factor for a breast cancer with poor prognosis.

The current edge-cutting research is focused on an irreversible third-generation EGFR inhibitor. The patent application CN201410365911.4 discloses the following compound of formula (I), which compound has a substantially higher inhibition activity to the EGFR activating mutation (such as exon 19 deletion activating mutation, or L858R activating mutation) and T790M resistance mutation than the inhibition activity to the wild-type EGFR (WT EGFR), with a good selectivity, a relatively low toxicity side-effect and a good safety.

(I)

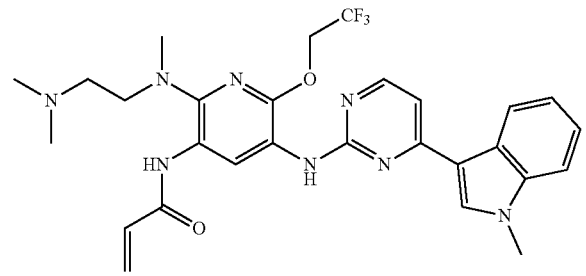

A crystalline form has some influence on the physical properties of the compounds. Due to the different crystal lattice structures, a pharmaceutical compounds showing polymorphs may have not only different appearances such as color and shape, but also different physical properties such as melting point, solubility, density, stability, hygroscopicity and the like, resulting in that they show different dissolution and absorption behaviors in vivo. This might have influence on the clinically therapeutical effect and safety of the pharmaceutical compounds to a certain extent.

Specific crystalline form will have a different thermodynamic behavior as compared to amorphous or another crystalline form. Melting point apparatus, thermogravimetric analysis (TGA) or differential scanning calorimetry (DSC) or the like can be used in laboratories to measure the thermal properties, to differentiate a certain specific crystalline form from an amorphous and another crystalline form. Specific crystalline forms may have special spectral properties. For example, the data of both X-ray powder diffraction pattern and IR spectra can characterize specific crystalline forms.

SUMMARY OF THE INVENTION

A technical problem to be solved by the present invention is to provide a mesylate salt of the compound of formula (I) in crystal form, the preparation method thereof, a pharmaceutical composition containing the crystal form, and the use of the crystal form in treating diseases mediated by activating and resistance mutations of EGFR, in particular cancer, in mammal, in particular in human.

In one aspect of the present invention there is provided Form I of the mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide represented by formula (I), which is named herein as Form I, (I)

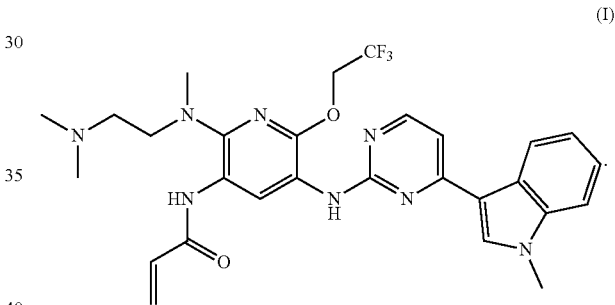

Form I may be characterized by peaks in X-ray powder diffraction pattern at the following diffraction angles (2θ values) of: 4.58°±0.2°, 14.08°±0.2°, 15.00°±0.2°, 16.40°±0.2°, 17.84°±0.2°, 18.30°±0.2°, 20.26°±0.2°, 21.10°±0.2°, 21.88°±0.2°, 22.66°±0.2°, 25.58°±0.2°, 26.78°±0.2°.

Further, Form I may be characterized by an X-ray powder diffraction pattern (XRPD) as shown in FIG. 1.

Further, Form I may be characterized by an endothermic peak upon heating up to 212.6° C., and a differential scanning calorimetry (DSC) pattern as shown in FIG. 3.

Further, Form I may be characterized by a weight loss of about 1% upon heating up to 230° C., and a thermogravimetric analysis (TGA) pattern as shown in FIG. 5.

In another aspect of the present invention there is provided a method for preparing Form I of the mesylate salt of compound (I), comprising:
a) suspending the compound of formula (I) in a first solvent,
b) warming the mixture up to 20-70° C., and dropwisely adding a solution of methanesulfonic acid dissolved in a second solvent,
c) crystallizing and filtering to give Form I.

Further, the first solvent may be water, ketone, cyclic ether or nitrile solvent, or a mixed solvent thereof; and the second solvent may be water, ketone, cyclic ether or nitrile solvent, or a mixed solvent thereof. Further, the first solvent may be a mixed solvent of water and ketone, cycllic ether or nitrile solvent; and the second solvent may be ketone, cyclic ether or nitrile solvent, or a mixed solvent of water and ketone, cyclic ether or nitrile solvent. Further, the ketone solvent may include but is not limited to acetone, and the cyclics ether solvent may include but is not limited to teterhydrofuran or 1,4-dioxane, and the nitrile solvent may include but is not limited to acetonitrile.

Further, in the mixed solvent of ketone, cyclic ether or nitrile solvent and water, the ratio in volume of ketone, cyclic ether or nitrile solvent to water may be 10:1-25:1, and further, the ratio in volume of ketone, cyclic ether or nitrile solvent to water may be 15:1-19:1.

Further, in the step b), the mixture may be warmed up to 35-55° C.

In another aspect of the present invention there is provided a method for preparing Form I of the mesylate salt of compound (I), comprising:

a) suspending the compound of formula (I) in a first solvent, b) warming the mixture up to 20-70° C., and dropwisely adding a solution of methanesulfonic acid dissolved in a second solvent, c) dropwisely adding a third solvent, d) crystallizing and filtering to give Form I.

Further, the first solvent may be water, or ketone, cyclic ether or nitrile solvent, or a mixed solvent thereof; and the second solvent may be water, or ketone, cyclic ether or nitrile solvent, or a mixed solvent thereof. Further, the first solvent may be a mixed solvent of water and ketone, cyclic ether or nitrile solvent; and the second solvent may be ketone, cyclic ether or nitrile solvent, or a mixed solvent of water and ketone, cyclic ether or nitrile solvent. Further, the ketone solvent may include but is not limited to acetone, and the cyclic ether solvent may include but is not limited to teterhydrofuran or 1,4-dioxane, and the nitrile solvent may include but is not limited to acetonitrile.

Further, in the mixed solvent of ketone, cyclic ether or nitrile solvent and water, the ratio in volume of ketone, cyclic ether or nitrile solvent to water may be 10:1-25:1, and further, the ratio in volume of ketone, cyclic ether or nitrile solvent to water may be 15:1-19:1.

Further, in Step b), the mixture may be warmed up to 35-55° C.

Further, the third solvent may be $C_{6-7}$ alkane, ether or ester solvent. Further, the $C_{6-7}$ alkane solvent may include but is not limited to n-heptane; and the ether solvent may include but is not limited to methyl t-butyl ether; and the ester solvent may include but is not limited to methyl formate, ethyl acetate, isopropyl acetate, propyl acetate or butyl acetate.

In yet another aspect of the present invention there is provided Form II of the mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide represented by formula (I), which is named herein as Form II,

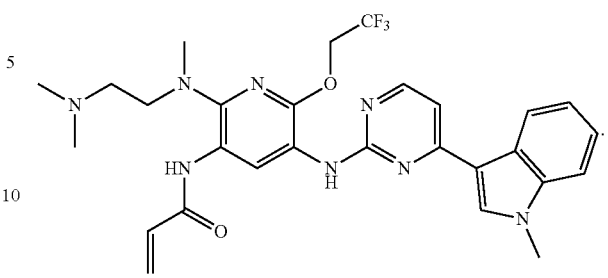

Form II may be characterized by peaks in X-ray powder diffraction pattern at the following diffraction angles (2θ values) of: 6.94°±0.2°, 11.24°±0.2°, 11.94°±0.2°, 14.72°±0.2°, 18.74°±0.2°, 19.38°±0.2°, 20.22°±0.2°, 22.10°±0.2°, 22.92°±0.2°, 24.48°±0.2°, 25.14°±0.2°, 26.42°±0.2°.

Further, Form II may be characterized by an X-ray powder diffraction (XRPD) pattern as shown in FIG. 2.

Further, Form II may be characterized by an endothermic peak upon heating up to 206.8° C., and a differential scanning calorimetry (DSC) pattern as shown in FIG. 4.

Further, Form II may be characterized by a weight loss of about 0.95% upon heating up to 220° C., and a thermogravimetric analysis (TGA) pattern as shown in FIG. 6.

In another aspect of the present invention there is provided a method for preparing Form II of the mesylate salt of compound (II), comprising dissolving Form I of the mesylate salt of the compound of formula (I) in an alcohol solvent under heating condition, cooling, crystallizing, and filtering to give Form II.

Further, the alcohol solvent may include but is not limited to methanol or ethanol.

In the crystal forms of the mesylate salt of the compound of formula (I), the ratio of the compound of formula (I) to methanesulfonic acid may be 1:1.

In some embodiments, the present invention provides a pharmaceutical composition, comprising Form I of the mesylate salt of the compound of formula (I).

In some embodiments, the present invention provides a pharmaceutical composition, comprising Form II of the mesylate salt of the compound of formula (I).

In some embodiments, the present invention provides a pharmaceutical composition, comprising a mixture of Form I and Form II of the mesylate salt of the compound of formula (I).

In some embodiments, the present invention further provides a pharmaceutical composition, comprising Form I of the mesylate salt of the compound of formula (I), and a pharmaceutically acceptable carrier, excipient or diluent.

In some embodiments, the present invention further provides a pharmaceutical composition, comprising Form II of the mesylate salt of the compound of formula (I), and a pharmaceutically acceptable carrier, excipient or diluent.

In some embodiments, the present invention further provides a pharmaceutical composition, comprising a mixture of Form I and Form II of the mesylate salt of the compound of formula (I), and a pharmaceutically acceptable carrier, excipient or diluent.

In some embodiments, the present invention provides the use of the pharmaceutical composition in manufacture of a medicament for treating cancer, wherein the pharmaceutical composition comprises Form I of, Form II of, or a mixture of Form I and Form II of the mesylate salt of the compound of formula (I).

In some embodiments, the present invention provides Form I of the mesylate salt of the compound of formula (I) for use in anti-tumor medicament.

In some embodiments, the present invention provides Form II of the mesylate salt of the compound of formula (I) for use in anti-tumor medicament.

In some embodiments, the present invention provides a mixture of Form I and Form II of the mesylate salt of the compound of formula (I) for use in anti-tumor medicament.

In some embodiments, the present invention also provides the use of Form I of the mesylate salt of the compound of formula (I) in manufacture of a medicament for treating cancers.

In some embodiments, the present invention also provides the use of Form I of the mesylate salt of the compound of formula (I) in manufacture of a medicament for treating diseases mediated by activating and resistance mutations of EGFR, in particular cancers in mammal, in particular human.

In some embodiments, the present invention also provides the use of Form II of the mesylate salt of the compound of formula (I) in manufacture of a medicament for treating cancers.

In some embodiments, the present invention also provides the use of Form II of the mesylate salt of the compound of formula (I) in manufacture of a medicament for treating diseases mediated by activating and resistance mutations of EGFR, in particular cancers in mammal, in particular human.

In some embodiments, the present invention also provides the use of a mixture of Form I and Form II of the mesylate salt of the compound of formula (I) in manufacture of a medicament for treating cancers.

In some embodiments, the present invention also provides the use of a mixture of Form I and Form II of the mesylate salt of the compound of formula (I) in manufacture of a medicament for treating diseases mediated by activating and resistance mutations of EGFR, in particular cancers in mammal, in particular human.

In some embodiments, the present invention also provides Form I of the mesylate salt of the compound of formula (I) for use in treating diseases mediated by activating and resistance mutations of EGFR, in particular cancers in mammal, in particular human.

In some embodiments, the present invention also provides Form II of the mesylate salt of the compound of formula (I) for use in treating diseases mediated by activating and resistance mutations of EGFR, in particular cancers in mammal, in particular human.

In some embodiments, the present invention also provides a mixture of Form I and Form II of the mesylate salt of the compound of formula (I) for use in treating diseases mediated by activating and resistance mutations of EGFR, in particular cancers in mammal, in particular human.

In some embodiments, the present invention also provides a method for treating diseases mediated by activating and resistance mutations of EGFR, in particular cancers in mammal, in particular human, including administering to a subject Form I of the mesylate salt of the compound of formula (I), or a pharmaceutical composition comprising a therapeutically effective amount of Form I of the mesylate salt of the compound of formula (I) and a pharmaceutically acceptable carrier, excipient or diluent.

In some embodiments, the present invention also provides a method for treating diseases mediated by activating and resistance mutations of EGFR, in particular cancers in mammal, in particular human, including administering to a subject Form II of the mesylate salt of the compound of formula (I), or a pharmaceutical composition comprising a therapeutically effective amount of Form II of the mesylate salt of the compound of formula (I) and a pharmaceutically acceptable carrier, excipient or diluent.

In some embodiments, the present invention also provides a method for treating diseases mediated by activating and resistance mutations of EGFR, in particular cancers in mammal, in particular human, including administering to a subject a mixture of Form I and Form II of the mesylate salt of the compound of formula (I), or a pharmaceutical composition comprising a therapeutically effective amount of a mixture of Form I and Form II of the mesylate salt of the compound of formula (I) and a pharmaceutically acceptable carrier, excipient or diluent.

The cancer as mentioned herein includes but is not limited to, for example, lung cancer, ovarian cancer, cervical cancer, breast cancer, stomach cancer, colorectal cancer, pancreatic cancer, glioma, glioblastoma, melanoma, prostate cancer, leukemia, lymphoma, non-Hodgkin's lymphoma, hepatocellular cancer, gastrointestinal stromal tumor (GIST), thyroid cancer, cholangiocarcinoma, endometrial cancer, renal cancer, anaplastic large cell lymphoma, acute myeloid leukemia (AML), multiple myeloma, and mesothelioma. In particular, the present invention in at least some embodiments has a good effect on the cancers having a mutation of the epidermal growth factor receptor, which mutation substitutes a threonine with a methionine at position 790 (EGFR T790M). For example, the present crystal forms of the mesylate salt of the compound of formula (I) can be used as a drug for treating the non-small cell lung cancer (EGFR T790M).

Form I of, Form II of, or the mixture of Form I and Form II of the mesylate salt of the compound of formula (I) may be administered to mammal including human, and can be administrated orally, rectally, parenterally (intravenously, intramuscularly or subcutaneously), topically (such as in the form of powders, ointments or drops), or intratumorally.

Form I of, Form II of, or the mixture of Form I and Form II of the mesylate salt of the compound of formula (I) may be administered at a dosage of about 0.05-50 mg/kg body weight/day, for example 0.1-45 mg/kg body weight/day, in a further example, 0.5-35 mg/kg body weight/day.

Form I of, Form II of, or the mixture of Form I and Form II of the mesylate salt of the compound of formula (I) may be formulated into the solid dosage forms for oral administration, including but not limited to capsules, tablets, pills, powders, granules or the like. In these solid dosage forms, the mesylate salts of the compound of formula (I) as active ingredients may be admixed with at least one conventional inert excipients (or carriers), such as sodium citrate or dicalcium phosphate, or admixed with the following ingredients: (1) fillers or extenders, such as starch, lactose, sucrose, glucose, mannitol and silicic acid or the like; (2) binders, such as hydroxymethylcellulose, aginate, gelatin, polyvinylpyrrolidone, sucrose and arabic gum or the like; (3) humectants, such as, glycerol or the like; (4) disintegrating agents, such as agar, calcium carbonate, potato starch or tapioca starch, alginic acid, certain composite silicate, and sodium carbonate or the like; (5) retarding agents, such as paraffin wax or the like; (6) absorption enhancers, such as, quaternary ammonium compounds or the like; (7) moistening agents, such as cetanol and glyceryl monostearate or the like; (8) absorbents, such as, kaolin or the like; and (9)

lubricants, such as, talc, calcium stearate, magnesium stearate, solid polyethylene glycol, sodium dodecyl sulphate or the like, or mixtures thereof. Capsules, tablets and pills may also comprise buffers.

Said solid dosage forms such as tablets, sugar pills, capsules, pills and granules can also be coated or microencapsulated by coatings and shell materials such as enteric coatings and other materials well known in the art. They may comprise opacifiers, and the release of active ingredients in these compositions may be carried out in a certain portion of digestive tract in a retarded manner. The examples for embedding components that may be adopted are polymer-based and wax-based substances. If necessary, active ingredients can also be formulated into the form of microcapsules with one or more of the above excipients.

Form I of, Form II of, or the mixture of Form I and Form II of the mesylate salt of the compound of formula (I) may be formulated into liquid dosage forms for oral administration, including but not limited to pharmaceutically acceptable emulsions, solutions, suspensions, syrups and tinctures or the like. Besides, Form I of, Form II of, or a mixture of Form I and Form II of the mesylate salt of the compound of formula (I) as active ingredients, the liquid dosage forms may comprise inert diluents customarily used in the art, such as water and other solvents, solubilizers and emulsifiers, such as, ethanol, isopropanol, ethyl carbonate, ethyl acetate, propylene glycol, 1,3-butanediol, dimethyl formamide, and oils, especially cottonseed oil, peanut oil, corn germ oil, olive oil, castor oil and sesame oil and the like, or the mixtures thereof, and the like. Besides these inert diluents, the liquid dosage forms may also comprise conventional adjuvants, such as moistening agents, emulsifiers and suspending agents, sweeting agents, flavoring agents and fragrances and the like.

Said suspending agents includes, such as, ethoxylated isostearyl alcohol, polyoxyethylene sorbitol and sorbitan ester, microcrystalline cellulose, aluminium methoxide and agar and the like or the mixtures thereof.

Form I of, Form II of, or the mixture of Form I and Form II of the mesylate salt of the compound of formula (I) may be formulated into dosage forms for parenteral injection, including but not limited tophysiologically acceptable sterile aqueous or non-aqueous solutions, dispersions, suspensions or emulsions, and sterile powder for re-dissolving into sterile injectable solutions or dispersions. Suitable carriers, diluents, solvents or excipients include water, ethanol, polyhydric alcohol and suitable mixtures thereof.

The compound of formula (I) or a pharmaceutically acceptable salt thereof can also be formulated into dosage forms for topical administration, including but not limited to ointments, powders, suppositories, drops, propellants and inhalants and the like. Form I of, Form II of, or the mixture of Form I and Form II of the mesylate salt of the compound of formula (I) as active ingredients are admixed together with physiologically acceptable carriers and optional preservatives, buffers, or if necessary, propellants, under sterile condition.

In some embodiments, the present invention also provides a pharmaceutical composition containing Form I of, Form II of, or the mixture of Form I and Form II of the mesylate salt of the compound of formula (I), and a pharmaceutically acceptable carrier, excipient or diluent. When preparing the pharmaceutical composition, Form I of, Form II of, or the mixture of Form I and Form II of the mesylate salt of the compound of formula (I) is generally admixed with the pharmaceutically acceptable carrier, excipient or diluent.

By conventional preparation methods, the composition may be formulated into conventional pharmaceutical preparations, such as tablets, pills, capsules, powders, granules, emulsions, suspensions, dispersions, solutions, syrups, elixirs, ointments, drops, suppositories, inhalants, propellants and the like.

Form I of, Form II of, or the mixture of Form I and Form II of the mesylate salt of the compound of formula (I) may be administered alone or in combination with other pharmaceutically acceptable therapeutic agents, especially with other anti-tumor drugs. The therapeutic agents include but are not limited to anti-tumor drugs which exert an effect on the chemical structure of DNA, such as cisplatin, anti-tumor drugs which affect the synthesis of nucleic acid, such as methotrexate (MTX), 5-fluorouracil (5FU) and the like, anti-tumor drugs which affect the transcription of nucleic acid, such as adriamycin, epirubicin, aclacinomycin, mitramycin and the like, anti-tumor drugs which exert an effect on synthesis of tubulin, such as paclitaxel, vinorelbine and the like, aromatase inhibitors such as aminoglutethimide, lentaron, letrozole, anastrozole and the like, inhibitors of the cell signal pathway such as epidermal growth factor receptor inhibitors imatinib, gefitinib, erlotinib, and the like. Each therapeutic agent to be combined can be administered simultaneously or sequentially, and can be administered either in a unitary formulation or in separate formulations. Such combination includes not only the combination of the compound of formula (I) with another active ingredient but also the combination of the compound with two or more other active ingredients.

The determination method for the absolute bioavailability of the intragastric administration of the crystal forms of the mesylate salt of the compound of formula (I) is as follows:

For intravenous administration: Healthy SD rats are randomly grouped. The tested substance is administered in a certain dosage D through the intravenous administration. The blood samples are collected through the retrobulbar venous plexus before the administration and 5 min, 15 min, 0.5 h, 1.0 h, 2.0 h, 4.0 h, 8.0 h, 12 h and 24 h after the administration, and separated to give plasmas. The concentration of the drug in plasma is determined with the liquid chromatography-tandem mass spectrometry method to give a drug concentration-time curve.

For intragastric administration: Healthy SD rats are randomly grouped. The tested substance is administered in a certain dosage D through the intragastric administration. The intravenous blood samples are collected through the rat's retrobulbar venous plexus before the administration and 0.5, 1.0, 2.0, 4.0, 6.0, 8.0, 10, 12 and 24 h after the administration, and separated to give plasmas. The concentration of the drug in plasma is determined with the liquid chromatography-tandem mass spectrometry method to give a drug concentration-time curve.

After dosage calibration, the absolute bioavailability F is calculated by the area under the drug concentration-time curve ($AUC_{0-t}$). The calculation equation is as follows:

$$F = (AUC_{intragastric} \times D_{intravenous}) / (AUC_{intravenous} \times D_{intragastric}) \times 100\%.$$

The solubilities of the crystal forms of the mesylate salt of the compound of formula (I) may be measured according to the following method:

Each substance is weighed in an appropriate amount and placed in a brown flask. Different solvents are added. The mixtures are ultrasonically treated for 20 seconds.

After the mixtures are uniformly dispersed, the mixtures are shaked at 25° C., 200 rpm for 24 h, then removed, and separated by centrifugation at 12000 rpm for 10 mins. The supernatants are removed by suction and diluted to a certain fold with the corresponding solvent. Then, the concentrations of the resulting solutions are determined by HPLC and their pH values are measured.

The beneficial technical effects produced by at least some embodiments of the present invention comprise:

Form I or Form II of the mesylate salt of the compound of formula (I) has been shown by tests to have an excellent in vivo bioavailability.

Form I or Form II of the mesylate salt of the compound of formula (I) has better solubilities in different pH solvents than the compound of formula (I).

Figure 1:
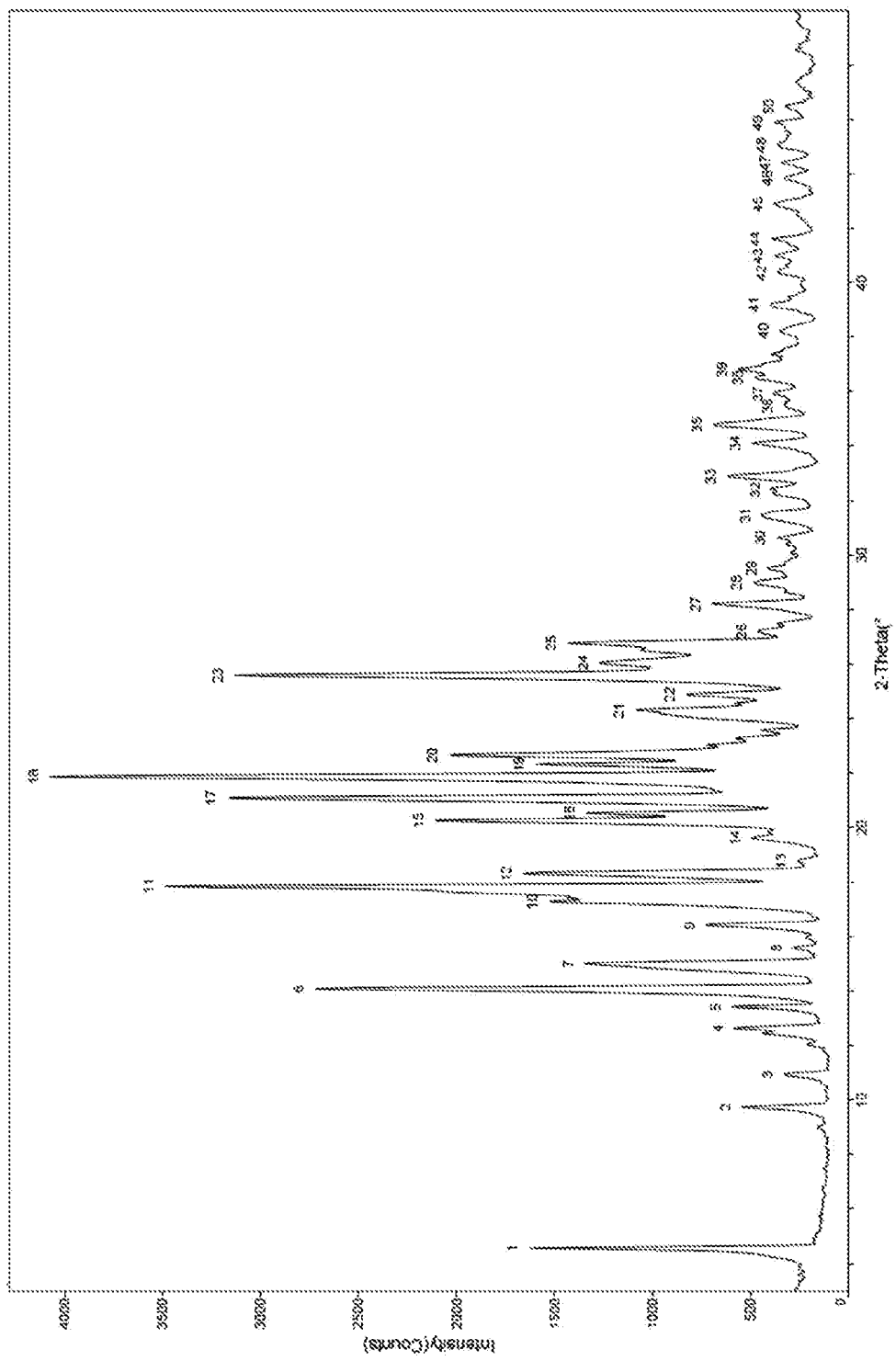
FIG. 1 is the XRPD pattern for Form I of the mesylate salt of the compound of formula (I).

The present invention will be further illustrated hereinafter in connection with specific Examples. It should be understood that these Examples are only used to illustrate the present invention by the way of examples without limiting the scope thereof. In the following examples, the experimental methods without specifying conditions are generally performed according to conventional conditions or based on the conditions recommended by the manufacturer. The parts and percentages are the parts and percentages by weight respectively, unless otherwise specified.

DETAILED DESCRIPTION OF THE INVENTION

The X-ray powder diffraction pattern disclosed herein was obtained with Panalytical Empyrean X-ray powder diffractometer. The parameters for the X-ray powder diffraction method disclosed herein are the following:

X-ray reflection parameters: Cu, Kα
Kα1(Å): 1.540598; Kα1(Å): 1.544426
Kα2/Kα1 intensity ratio: 0.50
Voltage: 45 kilovolts (kV)
Current: 40 milliamperes (mA)
Scanning range: from 3.0 to 50.0 degrees.

The differential scanning calorimetry (DSC) diagram disclosed herein was obtained with Perkin Elmer DSC 8500. The parameters for the differential scanning calorimetry method disclosed herein are the following:

Temperature controlling: the starting temperature is 50° C., and maintained at 50° C. for 1 min, and then the temperature is raised at a speed of 10° C./min to 250° C.

Protection gas: nitrogen.

The thermogravimetric analysis (TGA) pattern disclosed herein was obtained with NETZSCH TG 209 F3. The parameters for the thermogravimetric analysis method disclosed herein are the following:

Temperature controlling: maintained at 30° C. for 5 min, and then the temperature is raised at a speed of 10° C./min to 400° C.

Protection gas: nitrogen.

I. PREPARATION EXAMPLES

Example 1: N-{2-{[2-(dimethylamino)ethyl] (methyl)amino}-6-(2,2,2-trifluoroethoxy)-5-{[4-(1-methyl-1H-indol-3-yl)pyrimidin-2-yl] amino}pyridin-3-yl}acrylamide Intermediate 1c: $N^2$-methyl-$N^2$-[2-(dimethylamino) ethyl]-6-(2,2,2-trifluoroethoxy)-3-nitropyridine-2,5-di amine, the preparation method thereof referring to the example disclosed in the patent application No. CN201410365911.4.

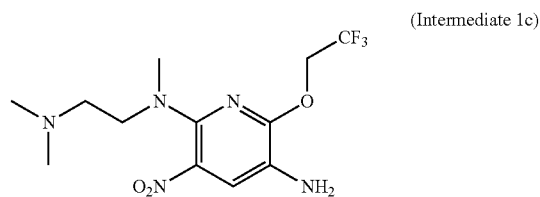 [SMILES: CN(C)CCN(C)c1nc(OCC(F)(F)F)c(N)cc1[N+](=O)[O-]]

(Intermediate 1c)

Intermediate 2a: 3-(2-chloropyrimidin-4-yl)-1-methyl-1H-indole, the preparation method thereof referring to the example disclosed in the patent application No. CN201410365911.4.

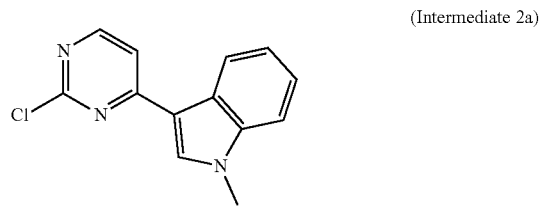 [SMILES: Cn1cc(-c2ccnc(Cl)n2)c2ccccc21]

(Intermediate 2a)

Compound (II): Synthesis of $N^2$-methyl-$N^2$-[2-(dimethylamino)ethyl]-6-(2,2,2-trifluoroethoxy)-$N^5$-[4-(1-methyl-1H-indol-3-yl)pyrimidin-2-yl]-3-nitropyridine-2,5-diamine

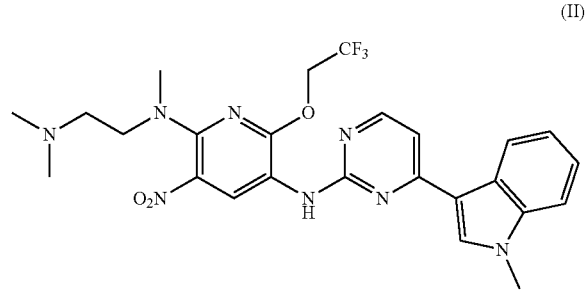 [SMILES: CN(C)CCN(C)c1nc(OCC(F)(F)F)c(Nc2nccc(-c3cn(C)c4ccccc34)n2)cc1[N+](=O)[O-]]

(II)

To a round bottom flask were added 3-(2-chloropyrimidin-4-yl)-1-methyl-1H-indole (73 mg, 0.3 mmol), N²-methyl-N²-[2-(dimethylamino)ethyl]-6-(2,2,2-trifluoroethoxy)-3-nitropyridine-2,5-di amine (100 mg, 0.3 mmol), tris(dibenzylideneacetone)dipalladium (14 mg, 0.015 mmol), 4,5-bis(diphenylphosphino)-9,9-dimethylxanthene (14 mg, 0.03 mmol), potassium phosphate (127 mg, 0.6 mmol) and 8 ml of dioxane. The mixture was reacted under the protection of argon gas at 95° C. for 5 hours, and filtered. The filtrate was evaporated under vacuum to dryness, and purified by a silica gel column chromatography (dichloromethane:methanol=20:1) to give 140 mg of the product in a yield of 86%. MS m/z: 545 [M+1].

Compound (III): Synthesis of N²-methyl-N²-[2-(dimethylamino)ethyl]-6-(2,2,2-trifluoroethoxy)-N⁵-[4-(1-methyl-1H-indol-3-yl)pyrimidin-2-yl]pyridine-2,3,5-triamine

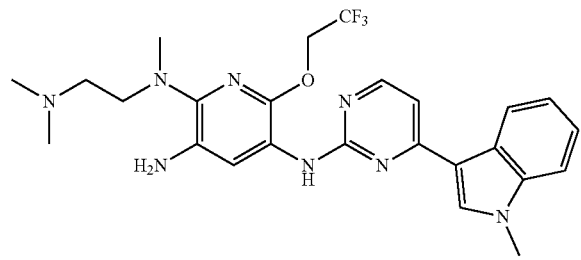

(III)

To a round bottom flask were added N²-methyl-N²[2-(dimethylamino)ethyl]-6-(2,2,2-trifluoroethoxy)-N⁵-[4-(1-methyl-1H-indol-3-yl)pyrimidin-2-yl]-3-nitropyridine-2,5-diamine (150 mg, 0.27 mmol), platinum dioxide (60 mg) and 10 ml of methanol. Then hydrogen was introduced. The mixture was reacted at room temperature for 1 h, filtered, and separated with a preparative plate (dichloromethane:methanol=10:1) to give 80 mg of the target compound in a yield of 56%. MS m/z: 515 [M+1].

Compound (I): Synthesis of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide

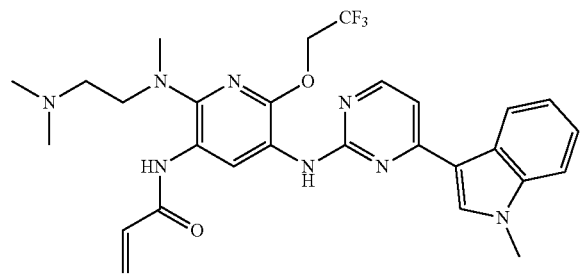

(I)

To a round bottom flask were added N²-methyl-N²[2-(dimethylamino)ethyl]-6-(2,2,2-trifluoroethoxy)-N⁵-[4-(1-methyl-1H-indol-3-yl)pyrimidin-2-yl]pyridine-2,3,5-triamine (80 mg, 0.16 mmol) and 5 ml of dichloromethane, and the mixture was cooled in an ice-water bath. 0.5N of a solution of acryloyl chloride in dichloromethane (0.5 ml, 0.25 mmol) was added. The resulting mixture was reacted in an ice-water bath for 1.5 hours, and diluted with 50 ml of ethyl acetate, and washed with a saturated sodium bicarbonate solution. The organic phase was dried with anhydrous sodium sulfate, and filtered. The filtrate was concentrated under vacuum, and purified by separation with a preparative plate (dichloromethane:methanol=10:1) to give 20 mg of the target product in a yield of 23%. MS m/z: 569 [M+1].

¹H NMR (400 MHz, DMSO-d6) δ 10.41 (s, 1H), 10.27 (s, 1H), 8.68 (s, 1H), 8.44 (s, 1H), 8.28 (t, J=8.5 Hz, 2H), 8.18 (s, 1H), 7.52 (d, J=8.0 hz, 1H), 7.29-7.14 (m, 3H), 6.98 (s, 1H), 6.28 (d, J=17.1 Hz, 1H), 5.76 (d, J=10.4 Hz, 1H), 5.00 (q, J=9.0 hz, 2H), 3.89 (s, 3H), 3.61 (s, 2H), 3.28 (s, 2H), 2.80 (s, 3H), 2.73 (s, 6H).

Example 2: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 10 L reaction vessel was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (451.5 g, 0.77 mol), and then added an aqueous acetone solution (5.42 L, the ratio in volume of two components is 15:1). The mixture was stirred, and after nitrogen replacement, warmed up to 35-40° C. A solution of methanesulfonic acid (74.2 g, 0.76 mol) in acetone (1.35 L) was added dropwisely. After the dropwise addition, the mixture was stirred for 15-18 hours at a controlled temperature of 35-40° C. Ethyl acetate (3.39 L) was added dropwisely. After the dropwise addition, the mixture was slowly cooled down to 20-25° C., and filtered. The filter cake was washed with ethyl acetate (0.45 L), and dried in vacuum at 50° C. for 40-48 hours to give Form I (409.9 g) in a yield of 80.09%.

¹H NMR (400 MHz, DMSO-d6) δ 9.80 (s, 1H), 9.23 (s, 1H), 8.53 (s, 1H), 8.42 (s, 1H), 8.30 (d, J=5.4 Hz, 2H), 8.23 (s, 1H), 7.52 (d, J=8.2 Hz, 1H), 7.25 (t, J=7.2 Hz, 1H), 7.22 (d, J=8.0 Hz, 1H), 7.15 (t, J=7.4 Hz, 1H), 6.70 (dd, J=17.0, 10.2 Hz, 1H), 6.34 (dd, J=17.0, 1.7 Hz, 1H), 5.83 (dd, J=10.3, 1.6 Hz, 1H), 5.02 (q, J=9.1 Hz, 2H), 3.88 (s, 3H), 3.65 (t, J=6.0 Hz, 2H), 3.33 (t, J=6.0 Hz, 2H), 2.86 (s, 6H), 2.81 (s, 3H), 2.44 (s, 3H).

Figure 3:
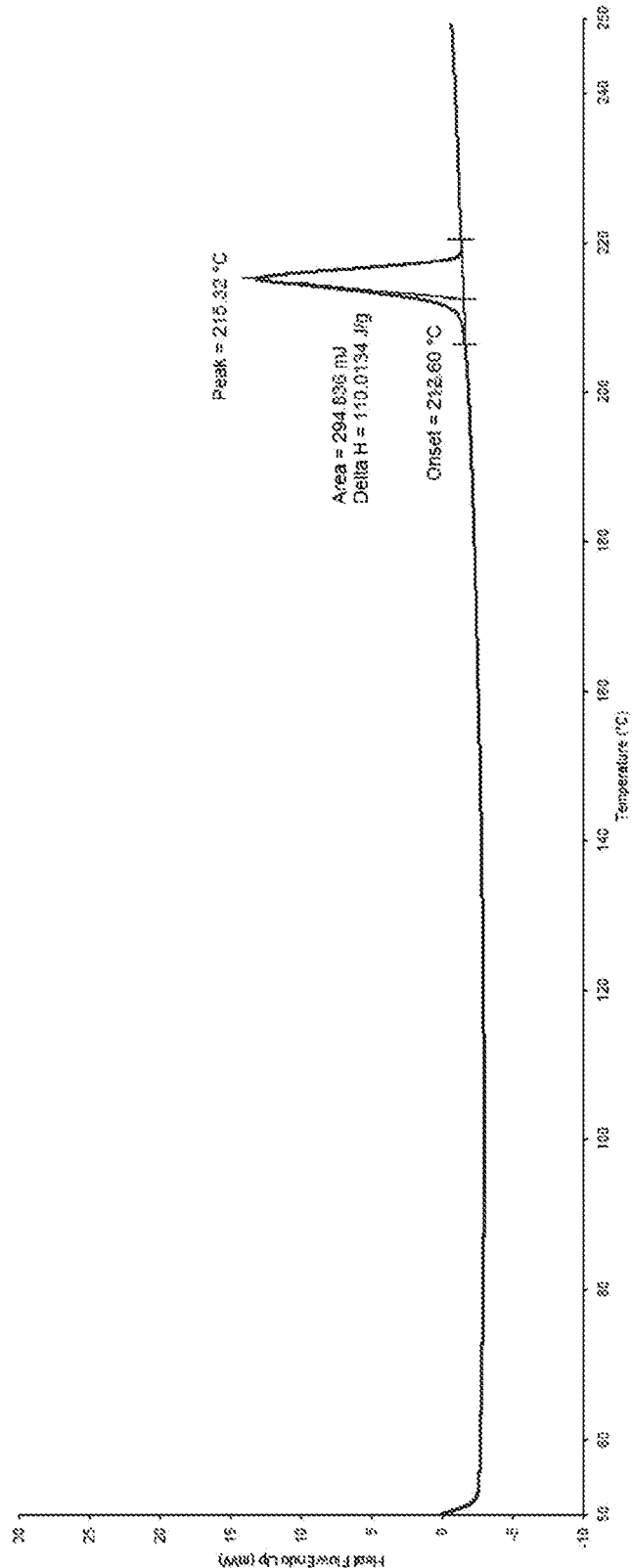
FIG. 3 is the DSC diagram for Form I of the mesylate salt of the compound of formula (I).
Figure 5:
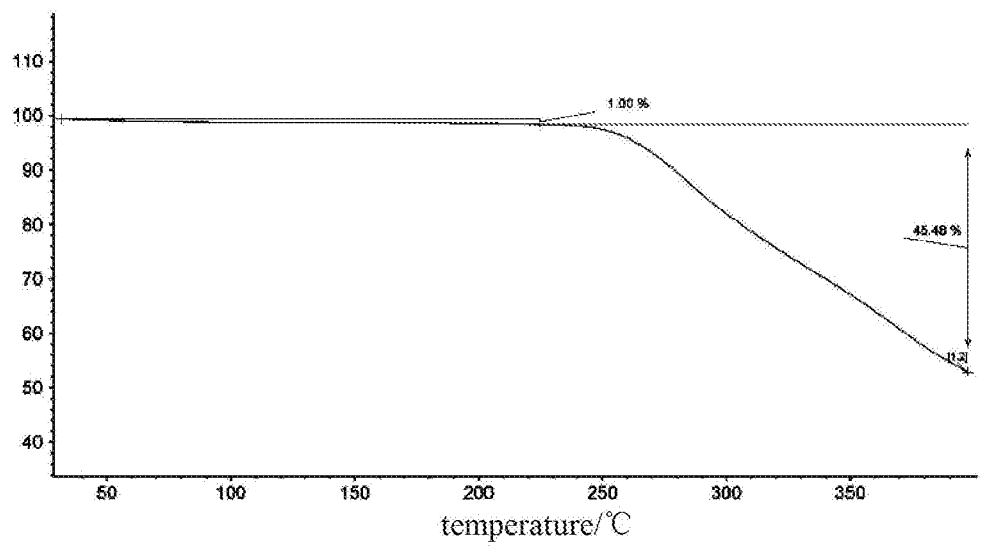
FIG. 5 is the TGA diagram for Form I of the mesylate salt of the compound of formula (I).

After testing, Form I obtained in this example had characteristic peaks in X-ray powder diffraction pattern at the following diffraction angles (2θ values) of: 4.58°±0.2°, 14.08°±0.2°, 15.00°±0.2°, 16.40°±0.2°, 17.84°±0.2°, 18.30°±0.2°, 20.26°±0.2°, 21.10°±0.2°, 21.88°±0.2°, 22.66°±0.2°, 25.58°±0.2°, 26.78°±0.2°; and its XRPD pattern is shown in FIG. 1, and its DSC diagram is shown in FIG. 3, and its TGA diagram is shown in FIG. 5.

Example 3: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous teterhydrofuran solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous teterhydrofuran solution (7.5 mL, the ratio in volume of two components is 19:1) was added dropwisely. After the dropwise addition, the mixture was stirred at a controlled temperature of 40-45° C. for 15-18 hours, then slowly cooled down to 20-25° C., and filtered. The filter cake was dried at 50° C. in vacuum for 40-48 hours to give Form I (3.4 g) in a yield of 57.95%.

Example 4: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous acetonitrile solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous acetonitrile solution (7.5 mL, the ratio in volume of two components is 19:1) was added dropwisely. After the dropwise addition, the mixture was stirred at a controlled temperature of 40-45° C. for 15-18 hours. Ethyl acetate (25 mL) was added dropwisely. After the dropwise addition, the mixture was slowly cooled down to 20-25° C., filtered, and dried in vacuum at 50° C. for 40-48 hours to give Form I (4.3 g) in a yield of 73.29%.

Example 5: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous teterhydrofuran solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous teterhydrofuran solution (7.5 mL, the ratio in volume of two components is 19:1) was added dropwisely. After the dropwise addition, the mixture was stirred at a controlled temperature of 40-45° C. for 15-18 hours. Ethyl acetate (25 mL) was added dropwisely. After the dropwise addition, the mixture was slowly cooled down to 20-25° C., filtered, and dried in vacuum at 50° C. for 40-48 hours to give Form I (4.75 g) in a yield of 80.96%.

Example 6: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous acetone solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous teterhydrofuran solution (7.5 mL, the ratio in volume of two components is 19:1) was added dropwisely. After the dropwise addition, the mixture was controlled at 40-45° C. Ethyl acetate (25 mL) was added dropwisely. After the dropwise addition, the mixture was slowly cooled down to 20-25° C., filtered, and dried in vacuum at 50° C. for 40-48 hours to give Form I (5.1 g) in a yield of 86.93%.

Example 7: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous teterhydrofuran solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous teterhydrofuran solution (7.5 mL, the ratio in volume of two components is 19:1) was added dropwisely. After the dropwise addition, the mixture was stirred at a controlled temperature of 40-45° C. for 15-18 hours. Isopropyl acetate (37.5 mL) was added dropwisely. After the dropwise addition, the mixture was slowly cooled down to 20-25° C., and filtered. The filter cake was washed with isopropyl acetate (5 mL). The mixture was slowly cooled down to 20-25° C., filtered, and dried in vacuum at 50° C. for 40-48 hours to give Form I (4.4 g) in a yield of 75.00%.

Example 8: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous acetone solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous teterhydrofuran solution (7.5 mL, the ratio in volume of two components is 19:1) was added dropwisely. After the dropwise addition, the mixture was controlled at 40-45° C. Ethyl formate (25 mL) was added dropwisely. After the dropwise addition, the mixture was slowly cooled down to 20-25° C., filtered, and dried in vacuum at 50° C. for 40-48 hours to give Form I (5.1 g) in a yield of 86.93%.

Example 9: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous acetone solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous teterhydrofuran solution (7.5 mL, the ratio in volume of two components is 19:1) was added dropwisely. After the dropwise addition, the mixture was controlled at 40-45° C. n-heptane (25 mL) was added dropwisely. After the dropwise addition, the mixture was slowly cooled down to 20-25° C., filtered, and dried in vacuum at 50° C. for 40-48 hours to give Form I (4.8 g) in a yield of 81.82%.

Example 10: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous acetonitrile solution (42.5 mL, the ratio in volume of two components is 19:1). The mixture was stirred, and after nitrogen replacement, warmed up to 40-45° C. Methanesulfonic acid (0.84 g, 8.7 mmol) in an aqueous acetonitrile solution (7.5 mL, the ratio in volume of two components is 19:1) was added dropwisely. After the dropwise addition, the mixture was stirred at a controlled temperature of 40-45° C. for 15-18 hours. The mixture was slowly cooled down to 20-25° C., filtered, and dried in vacuum at 50° C. for 40-48 hours to give Form I (4.0 g) in a yield of 68.18%.

Example 11: Preparation of Form I of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide (5 g, 8.8 mmol), and then added an aqueous acetonitrile solution (42.5 mL, the ratio in volume of two components is 19:1). The mixture was stirred, and after nitrogen replacement, warmed up to 40-45° C. Methanesulfonic acid (0.84 g, 8.7 mmol) in an acetonitrile solution (7.5 mL) was added dropwisely. After the dropwise addition, the mixture was controlled at 40-45° C. Methyl formate (355 mL) was added dropwisely. After the dropwise addition, the mixture was slowly cooled down to 20-25° C., filtered, and dried in vacuum at 50° C. for 40-48 hours to give Form I (4.5 g) in a yield of 76.70%.

Example 12: Preparation of Form II of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added Form I (5 g, 7.5 mmol) obtained according to Example 2, and then added methanol (50.0 mL). The mixture was stirred, warmed up to 50-55° C. The mixture was stirred at a controlled temperature of 50-55° C. for 15-18 hours, then slowly cooled down to 20-25° C., filtered, and dried in vacuum at 50° C. for 40-48 hours to give Form II (3.1 g) in a yield of 62.0%.

$^1$H NMR (400 MHz, DMSO-d6) δ 9.80 (s, 1H), 9.23 (s, 1H), 8.53 (s, 1H), 8.42 (s, 1H), 8.30 (d, J=5.4 Hz, 2H), 8.23 (s, 1H), 7.52 (d, J=8.2 Hz, 1H), 7.25 (t, J=7.2 Hz, 1H), 7.22 (d, J=8.0 Hz, 1H), 7.15 (t, J=7.4 Hz, 1H), 6.70 (dd, J=17.0, 10.2 Hz, 1H), 6.34 (dd, J=17.0, 1.7 Hz, 1H), 5.83 (dd, J=10.3, 1.6 Hz, 1H), 5.02 (q, J=9.1 Hz, 2H), 3.88 (s, 3H), 3.65 (t, J=6.0 hz, 2H), 3.33 (t, J=6.0 hz, 2H), 2.86 (s, 6H), 2.81 (s, 3H), 2.44 (s, 3H).

Figure 2:
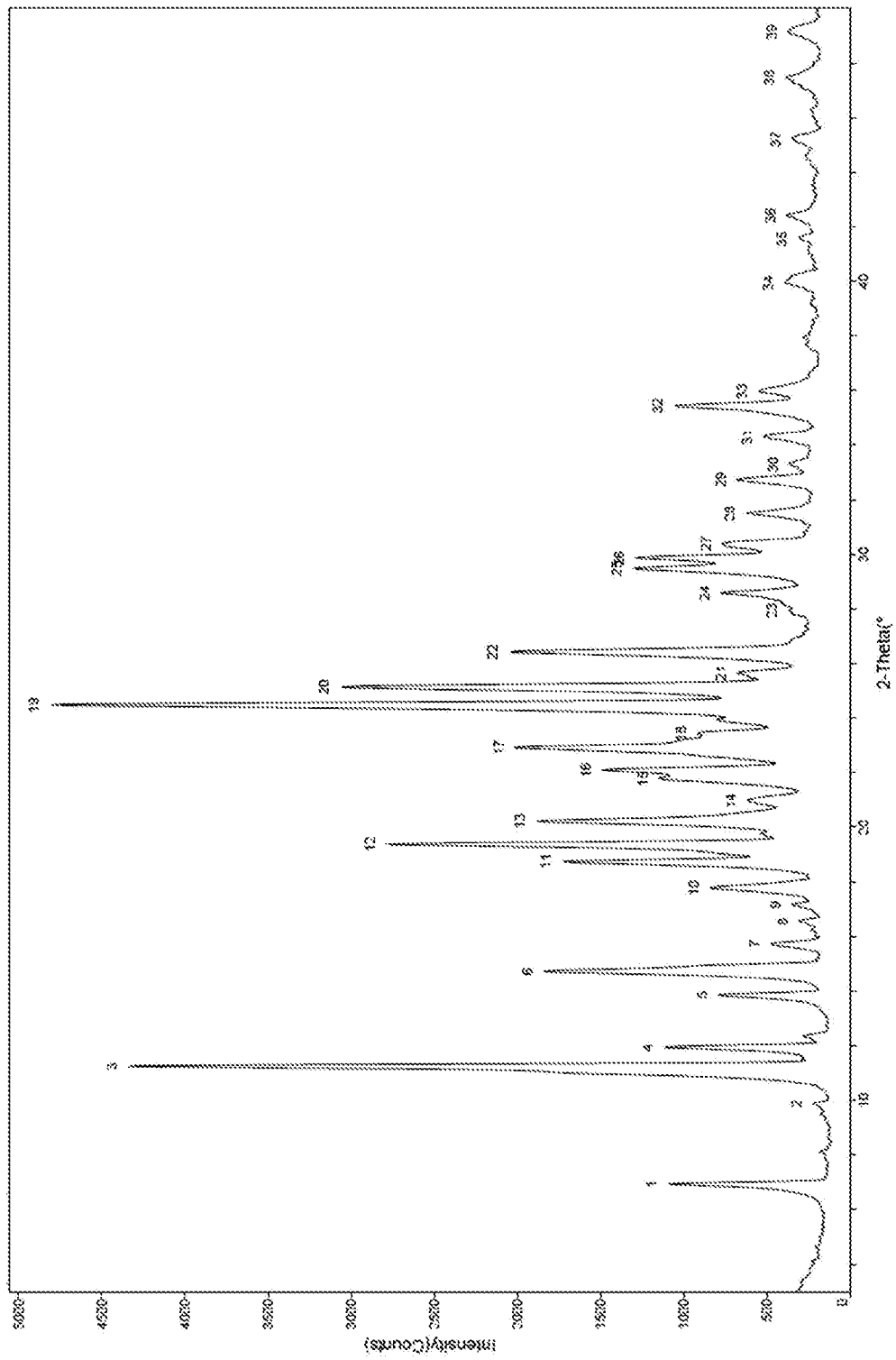
FIG. 2 is the XRPD pattern for Form II of the mesylate salt of the compound of formula (I).
Figure 4:
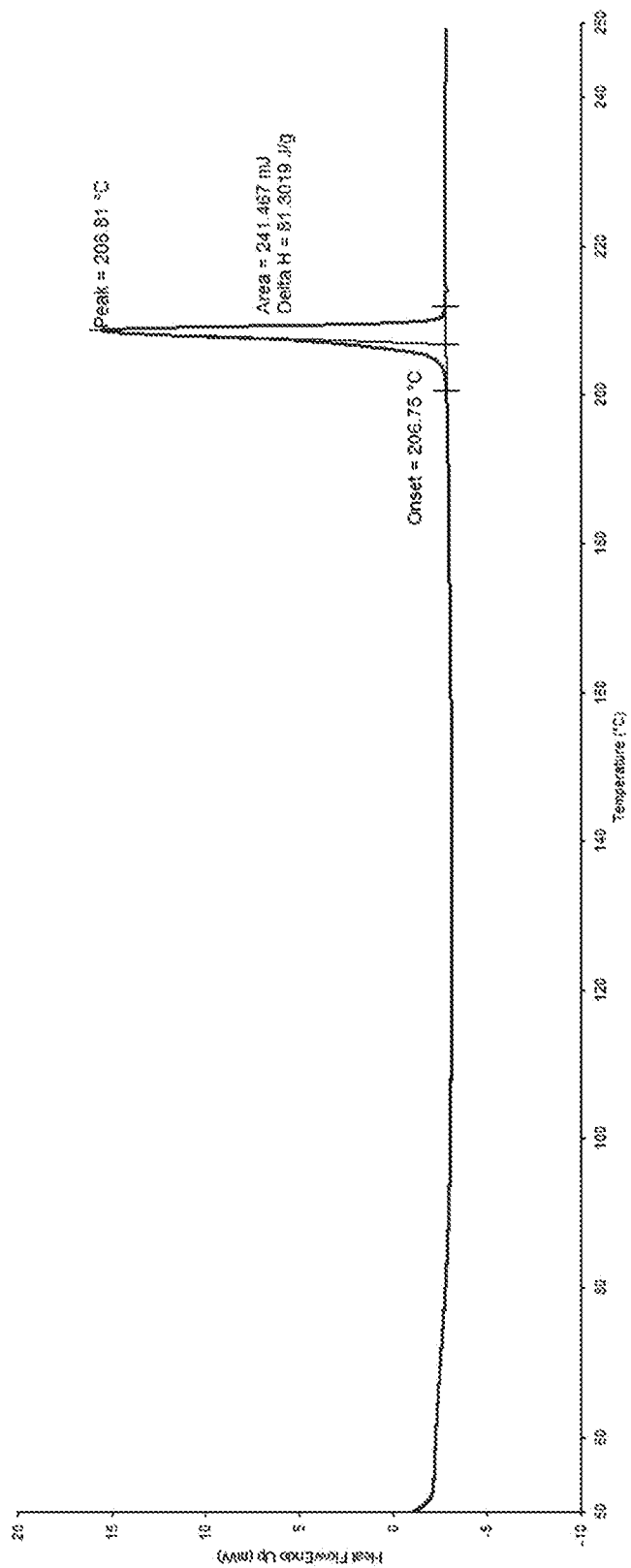
FIG. 4 is the DSC diagram for Form II of the mesylate salt of the compound of formula (I).
Figure 6:
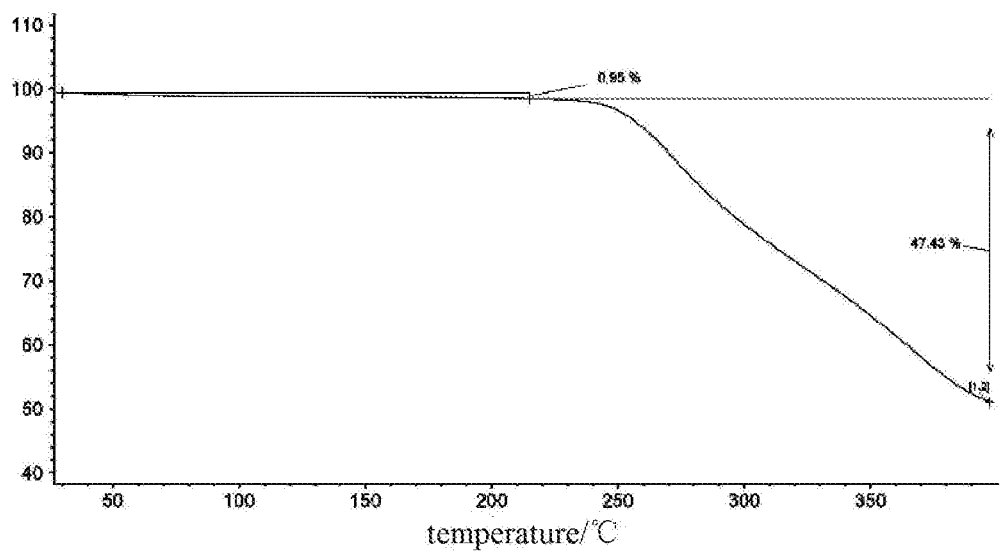
FIG. 6 is the TGA diagram for Form II of the mesylate salt of the compound of formula (I).

After testing, Form II obtained in this example had characteristic peaks in X-ray powder diffraction pattern at the following diffraction angles (2θ values) of: 6.94°±0.2°, 11.24°±0.2°, 11.94°±0.2°, 14.72°±0.2°, 18.74°±0.2°, 19.38°±0.2°, 20.22°±0.2°, 22.10°±0.2°, 22.92°±0.2°, 24.48°±0.2°, 25.14°±0.2°, 26.42°±0.2°; and its XRPD pattern is shown in FIG. 2, and its DSC diagram is shown in FIG. 4, and its TGA diagram is shown in FIG. 6.

Example 13: Preparation of Form II of the Mesylate Salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide To a 100 mL reaction bottle was added Form I (5 g, 7.5 mmol) obtained according to Example 2, and then added ethanol (50.0 mL). The mixture was stirred, warmed up to 50-55° C. The mixture was stirred at a controlled temperature of 50-55° C. for 15-18 hours, then slowly cooled down to 20-25° C., filtered, and dried in vacuum at 50° C. for 40-48 hours to give Form II (3.1 g) in a yield of 62.0%.

II. ACTIVITY TEST EXAMPLES

Test Example 1: Drug Absorption Experiments in SD Rats (Sprague Dawley Rats)

For intravenous administration: 20 healthy (half male and half female) SD rats with 200-280 g body weight, provided by Shanghai Sippr-BK laboratory animal Co. Ltd., were assigned randomly to 5 groups. Form I and Form II of the mesylate salt of the compound of formula (I), the compound of formula (I) of Example 1, and the compounds of Comparative Example 1 and Comparative Example 2 were intravenously administered in the dosage as shown in the following table. 0.2 ml of the intravenous blood samples were collected through the rat's retrobulbar venous plexus before the administration and 5 min, 15 min, 0.5 h, 1.0 h, 2.0 h, 4.0 h, 8.0 h, 12 h and 24 h after the administration, and separated to give plasmas.

The concentration of the drug in plasma was determined with the liquid chromatography-tandem mass spectrometry method to give a drug concentration-time curve.

The main pharmacokinetic parameters are shown in Table 1 below:

TABLE 1

| Parameters | Form I | Form II | Example 1 | Comparative Example 1 | Comparative Example 2 |
|---|---|---|---|---|---|
| Dosage D (mg/kg) | 2.5 | 2.5 | 2.5 | 3.0 | 4.0 |
| $C_{max}$ (ng/mL) | 104.7 | 125.4 | 81.3 | 327.5 | 630.2 |
| $AUC_{0-t}$ (ng · h/mL) | 307.9 | 362.0 | 307.3 | 437.8 | 810.7 |
| $T_{1/2}$ (h) | 4.73 | 4.83 | 3.96 | 2.72 | 1.71 |

In Table 1, the substance structure of Comparative Example 1 is shown below and was prepared according to Example 2 of the patent application CN201410365911.4.

(Comparative Example 1)

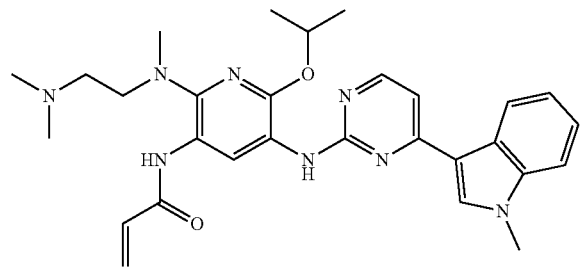

The substance structure of Comparative Example 2 is shown below and was prepared according to Example 16 of the patent application CN201410365911.4.

(Comparative Example 2)

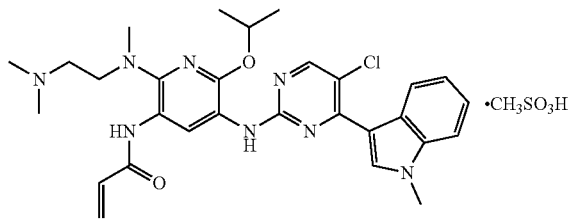

$T_{1/2}$: elimination half-life; $C_{max}$: maximum drug concentration in plasma; $AUC_{0-t}$: area under drug concentration-time curve.

For intragastric administration: 20 healthy (half male and half female) SD rats with 200-280 g body weight, provided by Shanghai Sippr-BK laboratory animal Co. Ltd., were assigned randomly to 5 groups. Form I and Form II of the mesylate salt of the compound of formula (I), the compound of formula (I) of Example 1, and the compounds of Comparative Example 1 and Comparative Example 2 were intragastrically administered in the dosage as shown in the following table. 0.2 ml of the intravenous blood samples were collected through the rat's retrobulbar venous plexus before the administration and 0.5, 1.0, 2.0, 4.0, 6.0, 8.0, 10, 12 and 24 h after the administration, and separated to give plasmas. The concentration of the drug in plasma was determined with the liquid chromatography-tandem mass spectrometry method to give a drug concentration-time curve.

Its main pharmacokinetic parameters are shown in Table 2:

| Parameters | Form I | Form II | Example 1 | Comparative Example 1 | Comparative Example 2 |
|---|---|---|---|---|---|
| Dosage D (mg/kg) | 10 | 10 | 10 | 6 | 10 |
| $C_{max}$ (ng/mL) | 45.3 | 36.7 | 17.6 | 12.63 | 28.3 |
| $AUC_{0-t}$ (ng·h/mL) | 613.2 | 566.3 | 231.7 | 77.66 | 172.2 |

-continued

| Parameters | Form I | Form II | Example 1 | Comparative Example 1 | Comparative Example 2 |
|---|---|---|---|---|---|
| $T_{1/2}$ (h) | 7.98 | 5.79 | 4.14 | 8.60 | 5.76. |
| F (%) | 49.8 | 39.1 | 18.85 | 8.9 | 8.5 |

In table 2, the structures and the preparation methods of Comparative Examples 1 and 2 are identical to those in Table 1.

After dosage calibration, the absolute bioavailability F was obtained by calculation of $AUC_{0-t}$. The calculation equation was as follows:

$$F = (AUC_{intragastric} \times D_{intravenous}) / (AUC_{intravenous} \times D_{intragastric}) \times 100\%.$$

The obtained absolute bioavailability F data are shown in the above table 2.

Conclusion: the absolute bioavailability for intragastric administration of Form I and Form II of the mesylate salt of the compound of formula (I) was remarkably better than the absolute bioavailability for intragastric administration of the compound of formula (I) according to Example 1, Comparative Example 1 and Comparative Example 2.

Test Example 2: Solubility Test

The compound of formula (I) of Example 1, Form I of the mesylate salt of the compound of formula (I), and Form II of the mesylate salt of the compound of formula (I) were investigated for the solubilities under different pH buffering solutions.

Test method: Each substance was weighed in an appropriate amount and placed in a brown flask. Different solvents were added. The mixtures were ultrasonically treated for 20 seconds. After the mixtures were uniformly dispersed, the mixtures were shaken at 25° C., 200 rpm for 24 h, then removed, and separated by centrifugation at 12000 rpm for 10 mins. The supernatants were removed by suction and diluted to a certain folds with the corresponding solvent. Then, the concentrations of the resulting solutions were determined by HPLC and their pH values were measured. The results are shown in the following table.

| Solvents | Compounds | | |
|---|---|---|---|
| | Example 1 | Form I | Form II |
| 0.1N HCl | >30 mg/ml | >100 mg/ml | >100 mg/ml |
| Acetate buffering solution at pH = 4.5 | 0.62 mg/ml | 29.05 mg/ml | 61.14 mg/ml |
| Phosphate buffering solution at pH = 6.8 | 0.0003 mg/ml | 0.02 mg/ml | 0.02 mg/ml |

Conclusion: when the solvent pH values were 1.0, 4.5 and 6.8, Form I and Form II of the mesylate salt of the compound of formula (I) had remarkably better solubilities than the compound of formula (I) of Example 1.

All of the literature mentioned herein are hereby incorporated by reference. It should be also noted that, upon reading the above mentioned contents of the present application, a person skilled in the art can modify, change or amend the present invention without departing from the spirit and scope of the present invention, and these equivalents are also within the scope as defined by the claims appended in the present application.

The invention claimed is:

1. Form I of the mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide represented by formula (I), wherein Form I has characteristic peaks in X-ray powder diffraction pattern at the following diffraction angles (2θ values) of: 4.58°±0.2°, 14.08°±0.2°, 15.00°±0.2°, 16.40°±0.2°, 17.84°±0.2°, 18.30°±0.2°, 20.26°±0.2°, 21.10°±0.2°, 21.88°±0.2°, 22.66°±0.2°, 25.58°±0.2°, 26.78°±0.2°,

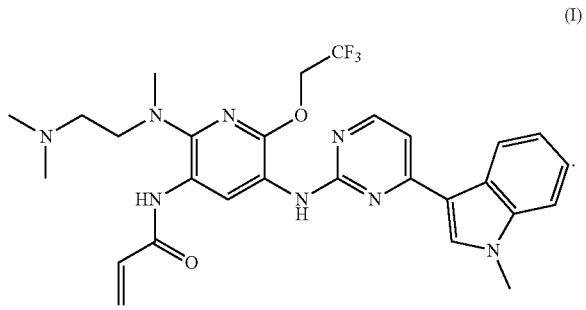 [SMILES: C=CC(=O)Nc1cc(Nc2nccc(-c3cn(C)c4ccccc34)n2)c(OCC(F)(F)F)nc1N(C)CCN(C)C]

(I)

2. Form I according to claim 1, which has an X-ray powder diffraction pattern that is substantially identical to that in FIG. 1.

3. A method for preparing Form I according to claim 1, comprising:
   a) suspending the compound of formula (I) in a first solvent,
   b) warming the mixture up to 20-70° C., and dropwisely adding a solution of methanesulfonic acid dissolved in a second solvent, and
   c) crystallizing and filtering to give Form I.

4. A method for preparing Form I according to claim 1, comprising:
   a) suspending the compound of formula (I) in a first solvent,
   b) warming the mixture up to 20-70° C., and dropwisely adding a solution of methanesulfonic acid dissolved in a second solvent,
   c) adding dropwisely a third solvent, and
   d) crystallizing and filtering to give Form I.

5. The method according to claim 3, wherein the first solvent is water, ketone, cyclic ether or nitrile solvent, or a mixed solvent thereof and the second solvent is water, ketone, cyclic ether or nitrile solvent, or a mixed solvent thereof.

6. The method according to claim 5, wherein the first solvent is a mixed solvent of water and ketone, cyclic ether or nitrile solvent; and the second solvent is ketone solvent, cyclic ether solvent or nitrile solvent, or a mixed solvent of water and ketone, cyclic ether or nitrile solvent.

7. The method according to claim 5, wherein the ketone solvent comprises acetone, and the cyclic ether solvent comprises tetrahydrofuran or 1,4-dioxane, and the nitrile solvent comprises acetonitrile.

8. The method according to claim 3, wherein in step b), warming the mixture up to 35-55° C.

9. The method according to claim 4, wherein the third solvent is $C_{6-7}$alkane, ether or ester solvent.

10. The method according to claim 9, wherein the $C_{6-7}$alkane solvent comprises n-heptane; and the ether solvent comprises methyl t-butyl ether; and the ester solvent comprises methyl formate, ethyl acetate, isopropyl acetate, propyl acetate or butyl acetate.

11. Form II of the mesylate salt of N-{2-{[2-(dimethylamino)ethyl](methyl)amino}-6-(2,2,2-trifluoroethoxy)-5-{[4-(1-methyl-1H-indol-3-yl)pyrimidin-2-yl]amino}pyridin-3-yl}acrylamide represented by formula (I), wherein Form II has characteristic peaks in X-ray powder diffraction pattern at the following diffraction angles (2θ values) of: 6.94°±0.2°, 11.24°±0.2°, 11.94°±0.2°, 14.72°±0.2°, 18.74°±0.2°, 19.38°±0.2°, 20.22°±0.2°, 22.10°±0.2°, 22.92°±0.2°, 24.48°±0.2°, 25.14°±0.2°, 26.42°±0.2°,

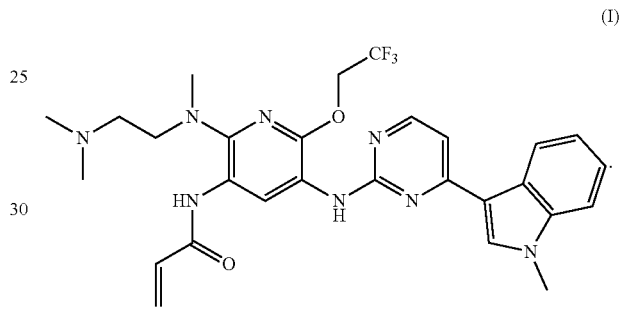

(I)

12. Form II according to claim 11, which has an X-ray powder diffraction pattern that is substantially identical to that in FIG. 2.

13. A method for preparing Form II according to claim 11, comprising dissolving Form I of the mesylate salt of the compound of formula (I) in alcohol solvent under heating, cooling, crystallizing, and filtering to give Form II.

14. The method according to claim 13, wherein said alcohol solvent comprises methanol or ethanol.

15. A pharmaceutical composition, comprising the form according to claim 1 and a pharmaceutically acceptable carrier.

16. A method of treating a patient suffering from cancers, the method comprising administering to the patient the Form I according to claim 1.

17. A pharmaceutical composition, comprising the form according to claim 11 and a pharmaceutically acceptable carrier.

18. A method of treating a patient suffering from cancers, the method comprising administering to the patient the Form II according to claim 11.

* * * * *